US008983593B2

(12) United States Patent
Bartol et al.

(10) Patent No.: US 8,983,593 B2
(45) Date of Patent: Mar. 17, 2015

(54) METHOD OF ASSESSING NEURAL FUNCTION

(75) Inventors: Stephen Bartol, Windsor (CA); Christopher Wybo, Royal Oak, MI (US)

(73) Assignee: Innovative Surgical Solutions, LLC, Wixom, MI (US)

(*) Notice: Subject to any disclaimer, the term of this patent is extended or adjusted under 35 U.S.C. 154(b) by 783 days.

(21) Appl. No.: 13/293,389

(22) Filed: Nov. 10, 2011

(65) Prior Publication Data
US 2013/0123659 A1    May 16, 2013

(51) Int. Cl.
*A61B 5/05*       (2006.01)
*A61B 5/11*       (2006.01)
*A61B 5/00*       (2006.01)

(52) U.S. Cl.
CPC ............. *A61B 5/1104* (2013.01); *A61B 5/4519* (2013.01); *A61B 5/6828* (2013.01); *A61B 5/4893* (2013.01)
USPC .......................................... 600/547; 600/554

(58) Field of Classification Search
USPC ................................. 600/547, 554
See application file for complete search history.

(56) References Cited

U.S. PATENT DOCUMENTS

| 3,200,814 A | 8/1965 | Taylor et al. |
| 3,565,080 A | 2/1971 | Ide et al. |
| 3,797,010 A | 3/1974 | Adler et al. |
| 4,817,628 A | 4/1989 | Zealear et al. |
| 5,284,153 A | 2/1994 | Raymond et al. |
| 5,284,154 A | 2/1994 | Raymond et al. |
| 5,775,331 A | 7/1998 | Raymond et al. |
| 6,324,432 B1 | 11/2001 | Rigaux et al. |
| 6,361,508 B1 | 3/2002 | Johnson et al. |
| 6,466,817 B1 | 10/2002 | Kaula et al. |
| 6,500,128 B2 | 12/2002 | Marino |
| 6,564,078 B1 | 5/2003 | Marino et al. |
| 6,760,616 B2 | 7/2004 | Hoey et al. |
| 6,807,438 B1 | 10/2004 | Brun Del Re et al. |
| 6,972,199 B2 | 12/2005 | Lebouitz et al. |
| 7,050,848 B2 | 5/2006 | Hoey et al. |
| 7,079,883 B2 | 7/2006 | Marino et al. |

(Continued)

FOREIGN PATENT DOCUMENTS

| EP | 1575010 A1 | 9/2005 |
| FR | 2920087 A1 | 2/2009 |

(Continued)

OTHER PUBLICATIONS

Bartol, Stephen MD, and Laschuk, Maria MD, "Arthroscopic Microscopic Discectomy in Awake Patients: The Effectiveness of Local/Neurolept Anaesthetic", Canadian Spine Society Meeting, Vernon, BC, Canada, Mar. 2002.

(Continued)

*Primary Examiner* — Devin Henson
(74) *Attorney, Agent, or Firm* — Quinn Law Group, PLLC.

(57) ABSTRACT

A method of determining a change in nerve function attributable to a surgical procedure includes assessing the nerve function via a first, induced mechanomyographic muscle response prior to the surgical procedure, and reassessing the nerve function via a second, induced mechanomyographic muscle response after the surgical procedure. Each mechanomyographic muscle response may be induced through an electrical stimulus provided directly to the nerve of the subject.

16 Claims, 10 Drawing Sheets

(56) References Cited

U.S. PATENT DOCUMENTS

| | | | |
|---|---|---|---|
| 7,177,677 B2 | 2/2007 | Kaula et al. | |
| 7,207,949 B2 | 4/2007 | Miles et al. | |
| 7,216,001 B2 | 5/2007 | Hacker et al. | |
| 7,236,832 B2 | 6/2007 | Hemmerling et al. | |
| 7,470,236 B1 | 12/2008 | Kelleher et al. | |
| 7,499,746 B2 * | 3/2009 | Buhlmann et al. | 607/2 |
| 7,522,953 B2 | 4/2009 | Kaula et al. | |
| 7,578,819 B2 | 8/2009 | Bleich et al. | |
| 7,582,058 B1 | 9/2009 | Miles et al. | |
| 7,657,308 B2 | 2/2010 | Miles et al. | |
| 7,664,544 B2 | 2/2010 | Miles et al. | |
| 7,668,588 B2 | 2/2010 | Kovacs | |
| 7,691,057 B2 | 4/2010 | Miles et al. | |
| 7,892,173 B2 | 2/2011 | Miles et al. | |
| 7,905,840 B2 | 3/2011 | Pimenta et al. | |
| 7,942,826 B1 | 5/2011 | Scholl et al. | |
| 7,959,577 B2 | 6/2011 | Schmitz et al. | |
| 7,962,191 B2 | 6/2011 | Marino et al. | |
| 7,981,058 B2 | 7/2011 | Akay | |
| 7,991,463 B2 | 8/2011 | Kelleher et al. | |
| 8,000,782 B2 | 8/2011 | Gharib et al. | |
| 8,016,776 B2 | 9/2011 | Bourget et al. | |
| 8,027,716 B2 | 9/2011 | Gharib et al. | |
| 8,055,349 B2 | 11/2011 | Gharib et al. | |
| 8,068,912 B2 | 11/2011 | Kaula et al. | |
| 8,075,499 B2 | 12/2011 | Nathan et al. | |
| 8,090,436 B2 | 1/2012 | Hoey et al. | |
| 8,133,173 B2 | 3/2012 | Miles et al. | |
| 8,137,284 B2 | 3/2012 | Miles et al. | |
| 8,147,421 B2 | 4/2012 | Farquhar et al. | |
| 8,165,653 B2 | 4/2012 | Marino et al. | |
| 8,343,065 B2 | 1/2013 | Bartol et al. | |
| 8,343,079 B2 | 1/2013 | Bartol et al. | |
| 2001/0031916 A1 | 10/2001 | Bennett et al. | |
| 2002/0038092 A1 | 3/2002 | Stanaland et al. | |
| 2002/0165590 A1 | 11/2002 | Crowe et al. | |
| 2003/0074037 A1 | 4/2003 | Moore et al. | |
| 2004/0077969 A1 | 4/2004 | Onda et al. | |
| 2004/0186535 A1 | 9/2004 | Knowlton | |
| 2004/0230138 A1 | 11/2004 | Inoue et al. | |
| 2004/0243018 A1 | 12/2004 | Organ et al. | |
| 2005/0075578 A1 | 4/2005 | Gharib et al. | |
| 2005/0085741 A1 | 4/2005 | Hoskonen et al. | |
| 2005/0102007 A1 | 5/2005 | Ayal et al. | |
| 2005/0240086 A1 | 10/2005 | Akay | |
| 2005/0245839 A1 | 11/2005 | Stivoric et al. | |
| 2005/0280531 A1 | 12/2005 | Fadem et al. | |
| 2005/0283204 A1 | 12/2005 | Buhlmann et al. | |
| 2006/0020177 A1 | 1/2006 | Seo et al. | |
| 2006/0052726 A1 | 3/2006 | Weisz et al. | |
| 2006/0135888 A1 | 6/2006 | Mimnagh-Kelleher et al. | |
| 2006/0270949 A1 | 11/2006 | Mathie et al. | |
| 2007/0038155 A1 | 2/2007 | Kelly, Jr. et al. | |
| 2007/0265675 A1 | 11/2007 | Lund et al. | |
| 2007/0276270 A1 | 11/2007 | Tran | |
| 2008/0051643 A1 | 2/2008 | Park et al. | |
| 2008/0058656 A1 | 3/2008 | Costello et al. | |
| 2008/0167695 A1 | 7/2008 | Tehrani et al. | |
| 2008/0234767 A1 | 9/2008 | Salmon et al. | |
| 2008/0287761 A1 | 11/2008 | Hayter et al. | |
| 2008/0306363 A1 | 12/2008 | Chaiken et al. | |
| 2008/0306397 A1 | 12/2008 | Bonmassar et al. | |
| 2008/0312560 A1 | 12/2008 | Jamsen et al. | |
| 2008/0312709 A1 | 12/2008 | Volpe et al. | |
| 2009/0036747 A1 | 2/2009 | Hayter et al. | |
| 2009/0062696 A1 | 3/2009 | Nathan et al. | |
| 2009/0069709 A1 * | 3/2009 | Schmitz et al. | 600/547 |
| 2009/0069722 A1 | 3/2009 | Flaction et al. | |
| 2009/0076336 A1 | 3/2009 | Mazar et al. | |
| 2009/0171381 A1 | 7/2009 | Schmitz et al. | |
| 2009/0192416 A1 | 7/2009 | Ernst et al. | |
| 2009/0228068 A1 | 9/2009 | Buhlmann et al. | |
| 2009/0247910 A1 | 10/2009 | Klapper | |
| 2009/0306741 A1 | 12/2009 | Hogle et al. | |
| 2009/0318779 A1 | 12/2009 | Tran | |
| 2010/0137748 A1 | 6/2010 | Sone et al. | |
| 2010/0152619 A1 | 6/2010 | Kalpaxis et al. | |
| 2010/0152622 A1 | 6/2010 | Teulings | |
| 2010/0152623 A1 | 6/2010 | Williams | |
| 2010/0168559 A1 | 7/2010 | Tegg et al. | |
| 2010/0292617 A1 | 11/2010 | Lei et al. | |
| 2011/0004207 A1 | 1/2011 | Wallace et al. | |
| 2011/0237974 A1 | 9/2011 | Bartol et al. | |
| 2012/0053491 A1 | 3/2012 | Nathan et al. | |

FOREIGN PATENT DOCUMENTS

| | | |
|---|---|---|
| WO | 0078209 A2 | 12/2000 |
| WO | 2007024147 A1 | 3/2007 |

OTHER PUBLICATIONS

Bartol, Stephen MD, and Laschuk, Maria MD, "Use of Nerve Stimulator to Localize the Spinal Nerve Root During Arthroscopic Discectomy Procedures", Canadian Spine Society Meeting, Vernon, BC, Canada, Mar. 2002.

Begg et al. "Computational Intelligence for Movement Sciences: Neural Networks and Other Emerging Techniques" 2006.

Bourke et al. "A Threshold-Based Fall-Detection Algorithm Using a Bi-Axial Gyroscope Sensor" Medical Engineering and Physics 30 (2008) 84-90.

Fee Jr., James W.; Miller, Freeman; Lennon, Nancy; "EMG Reaction in Muscles About the Knee to Passive Velocity, Acceleration, and Jerk Manipulations"; Alfred I. duPont Hospital for Children, Gait Laboratory, 1600 Rockland Road, Wilmington, DE 19899, United States Journal of Electromyography and Kinesiology 19 (2009) 467-475.

Koceja, D.M., Bernacki, R.H. and Kamen, G., "Methodology for the Quantitative Assessment of Human Crossed-Spinal Reflex Pathways," Medical & Biological Engineering & Computing, Nov. 1991, pp. 603-606, No. 6, US.

Tarata, M.; Spaepen, A.; Puers, R.; "The Accelerometer MMG Measurement Approach, in Monitoring the Muscular Fatigue"; Measurement Science Review; 2001; vol. 1, No. 1.

Murphy, Chris; Campbell, Niall; Caulfield, Brian; Ward, Tomas and Deegan, Catherine; "Micro Electro Mechanical Systems Based Sensor for Mechanomyography", 19th international conference Biosignal 2008, Brno, Czech Republic.

Nijsen, Tamara M.E.; Aarts, Ronald M.; Arends, Johan B.A.M.; Cluitmans, Pierre J.M.; "Model for Arm Movements During Myoclonic Seizures"; Proceedings of the 29th Annual International Conference of the IEEE EMBS Cite Internationale, Lyon, France Aug. 23-26, 2007.

Ohta, Yoichi; Shima, Norihiro; Yabe, Kyonosuke; "Superimposed Mechanomyographic Response at Different Contraction Intensity in Medial Gastrocnemius and Soleus Muscles"; International Journal of Sport and Health Science, vol. 5, 63-70, 2007.

* cited by examiner

*FIG. 4*
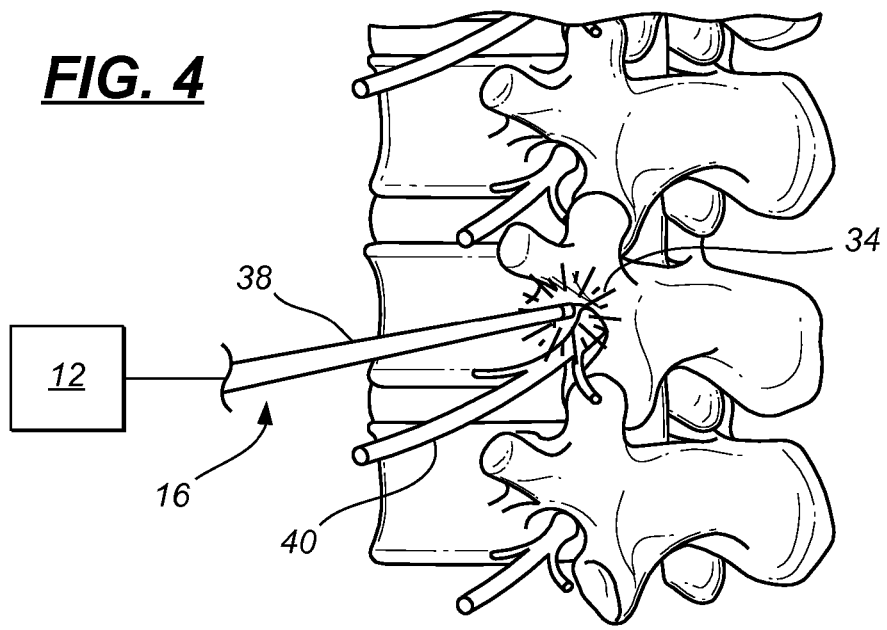
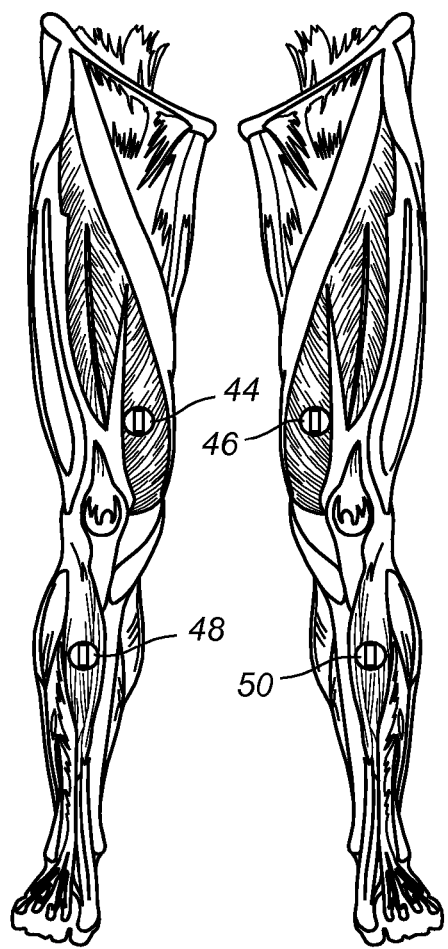
*FIG. 5*

METHOD OF ASSESSING NEURAL FUNCTION

TECHNICAL FIELD

The present invention relates generally to a device to assess differences and/or changes in neural function through mechanical sensing.

BACKGROUND

A neural impingement occurs when tissue near a nerve grows or swells into contact with the nerve. Many times, impinging tissue may pinch or compress the nerve against other structures within the body and reduce the nerve's ability to function properly. Neural impingements may often be caused by tumors, bone spurs, or soft tissue inflammation.

An impingement proximate the spinal column, e.g., a foraminal stenosis, may compress vital nerve roots as they exit the spinal column. For example, with a neural foraminal stenosis, the natural passageways (i.e., foramen) where the peripheral nerve roots exit the spine may become overgrown or otherwise restricted, and may compress/irritate the peripheral nerve root. Such irritation may result in pain and/or a loss of motor function in a limb innervated by that peripheral nerve. Other impingements may occur away from the spine. For example, in Carpal Tunnel Syndrome, the median nerve may be compressed as it passes through the carpal tunnel portion of the wrist. Other peripheral nerve compressions may include ulnar nerve compression at the elbow, nerve compression within the brachial plexus, pyriformis syndrome, or compression of any other peripheral motor nerve.

One manner of treating, for example, a spinal stenosis involves widening the foramen through surgical techniques. These procedures, such as a foraminotomy or a laminectomy, involve mechanically removing soft tissue or bone that may be impinging the neural tissue. This mechanical tissue removal may generally involve filing, cutting, and/or grinding procedures. By removing the overgrown tissue/bone, the nerve may decompress and ideally return to its normal function. Other procedures that may be used to decompress an impinged nerve may include: a discectomy (removal of all or a portion of a vertebral disc); removal of bone or disc fragments that may be compressing the nerve; removal of all or a portion of a tumor; removal of pus, fluid, or other material attributable to an infection; or removal of any other space occupying lesion or structure that may compress the nerve. Additionally, other indirect surgical procedures may be performed to decompress an impinged nerve. These may include, for example, a reduction of a spondylolysthesis; an interbody height restoration, e.g., through the insertion of a mechanical interbody spacer or bone graft; a reduction of a fracture; or an insertion of a device into interspinous space or into the facet joint space. Similar decompression techniques may likewise be performed to remove impingements against peripheral nerves.

Depending on the duration and degree of the compression, the nerve may either return to normal function following the decompression procedure or may have some degree of compromised function.

SUMMARY

A method of identifying a change in nerve function attributable to a surgical procedure includes assessing the nerve function prior to the surgical procedure, reassessing the nerve function after the surgical procedure. Assessing the nerve function may include providing a first electrical stimulus to a nerve of a subject, monitoring the mechanical motion of a muscle innervated by the nerve, and determining a first, minimum electrical stimulus operative to induce motion of the muscle. Likewise, reassessing the nerve function may include providing a second electrical stimulus to the nerve of the subject, monitoring the mechanical motion of the muscle innervated by the nerve, and determining a second, minimum electrical stimulus operative to induce motion of the muscle.

Once the nerve function has been assessed, and reassessed, the method may further include identifying a change in nerve function if the second, minimum electrical stimulus is different than the first, minimum electrical stimulus. In one configuration, each of the first electrical stimulus and the second electrical stimulus may respectively include a plurality of sequentially administered pulses, wherein each pulse is provided with a different electrical current magnitude. In this manner, each of the first and second, minimum electrical stimuli may respectively be the lowest electrical current magnitude operative to induce motion of the muscle.

When detecting an "induced" muscle motion, the system may compute a time derivative of acceleration (i.e., "jerk") from a mechanomyography signal received from a mechanical sensor in mechanical communication with the muscle of the subject, and may compare the computed time derivative of acceleration to a jerk threshold. If the jerk rate exceeds the threshold, the system may indicate that a muscle response was "induced."

In an embodiment, a surgical procedure may be performed between the assessing and the reassessing steps. The surgical procedure may be, for example, a decompression procedure operative to remove an impingement to the nerve. In this case, the first electrical stimulus and second electrical stimulus may respectively be provided to the nerve at a position upstream of the impingement.

Additionally, a related neurosurgical method may include affixing a mechanical sensor to the skin of a subject and in mechanical communication with a muscle innervated by a nerve, where the mechanical sensor is configured to monitor the motion of the muscle. The method may further include obtaining direct access to the nerve, wherein the nerve has an impingement, and electrically stimulating the nerve with a first electrical stimulus between the impingement and a spinal column of the subject. Using the mechanical sensor, a first, minimum electrical stimulus operative to induce motion of the muscle may be determined.

Following this initial testing of the nerve, the impingement to the nerve may be surgically removed. Once decompressed, the nerve may be electrically stimulated with a second electrical stimulus between the location of the removed impingement and the spinal column of the subject. The method may then include determining, from the mechanical sensor, a second, minimum electrical stimulus operative to induce motion of the muscle. A change in nerve function may be identified if the second, minimum electrical stimulus is different than the first, minimum electrical stimulus.

The above features and advantages and other features and advantages of the present invention are readily apparent from the following detailed description of the best modes for carrying out the invention when taken in connection with the accompanying drawings.

BRIEF DESCRIPTION OF THE DRAWINGS

FIG. 4 is a schematic side view of a treatment area including a lumbar spine.

FIG. 5 is a schematic illustration of a plurality of mechanical sensors in mechanical communication with various muscles of a subject.

DETAILED DESCRIPTION

Figure 1:
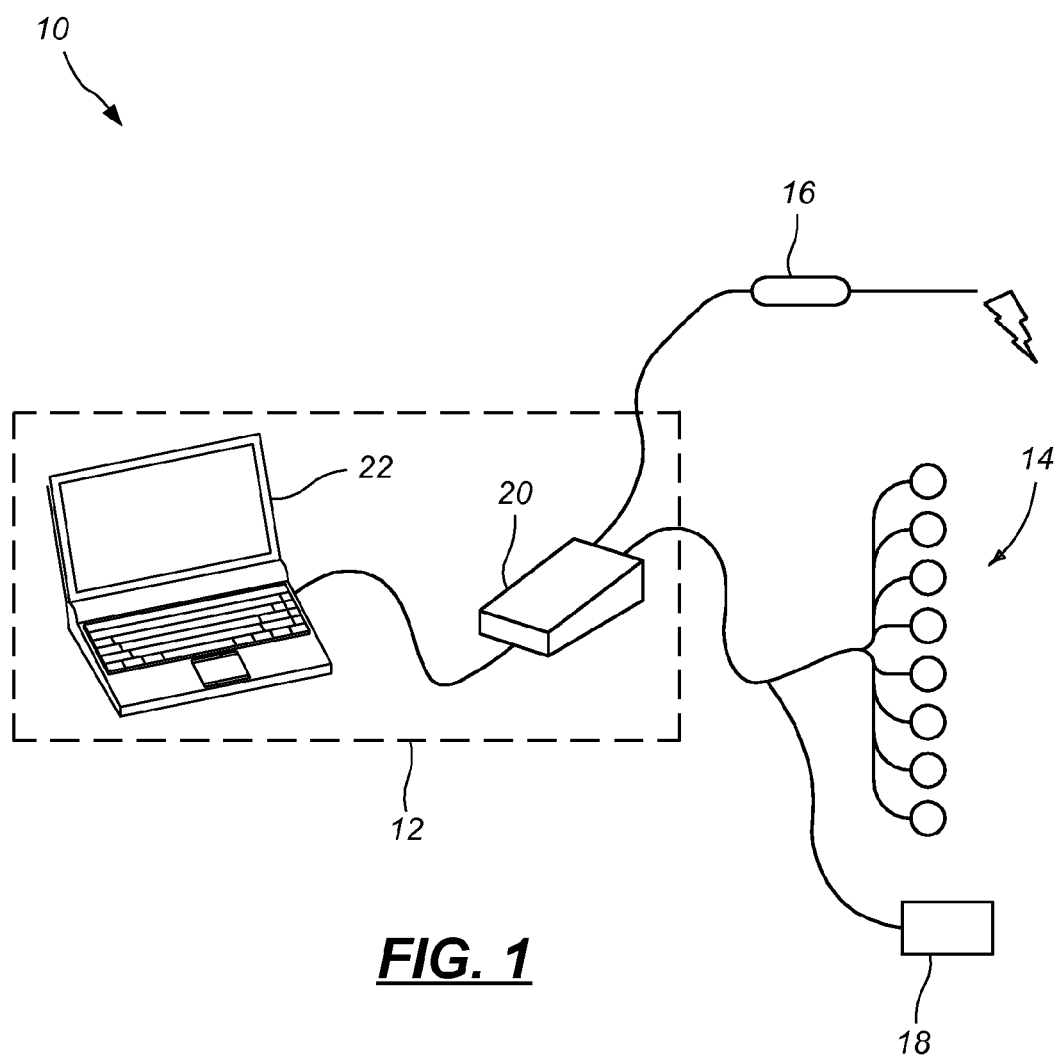
FIG. 1 is a schematic illustration of a mechanomyographic neural monitoring system.

Referring to the drawings, wherein like reference numerals are used to identify like or identical components in the various views, FIG. 1 schematically illustrates a neural monitoring system 10 (such as described in detail in U.S. patent application Ser. No. 12/040,515 to Bartol et al, titled "Minimally Invasive Nerve Monitoring Device and Method," which is incorporated herein by reference in its entirety). The neural monitoring system 10 may include a receiver 12 in communication with a plurality of sensing devices 14, a stimulator 16, and a ground patch 18. The receiver 12 may include, for example, a sensor interface 20 and a computing device 22. The computing device 22 may, in turn, include a processor, memory, and a display, and may be embodied as, for example, a personal computer, tablet computer, personal digital assistant (PDA), or the like. The sensor interface 20 may be configured to receive and present information from the plurality of sensing devices 14 to the computing device 22, and may include, for example, communications circuitry, signal processing circuitry, and/or other associated interfacing circuitry. While shown as distinct components in FIG. 1, in an embodiment, the sensor interface 20 may be an integral part of the computing device 22.

Figure 2:
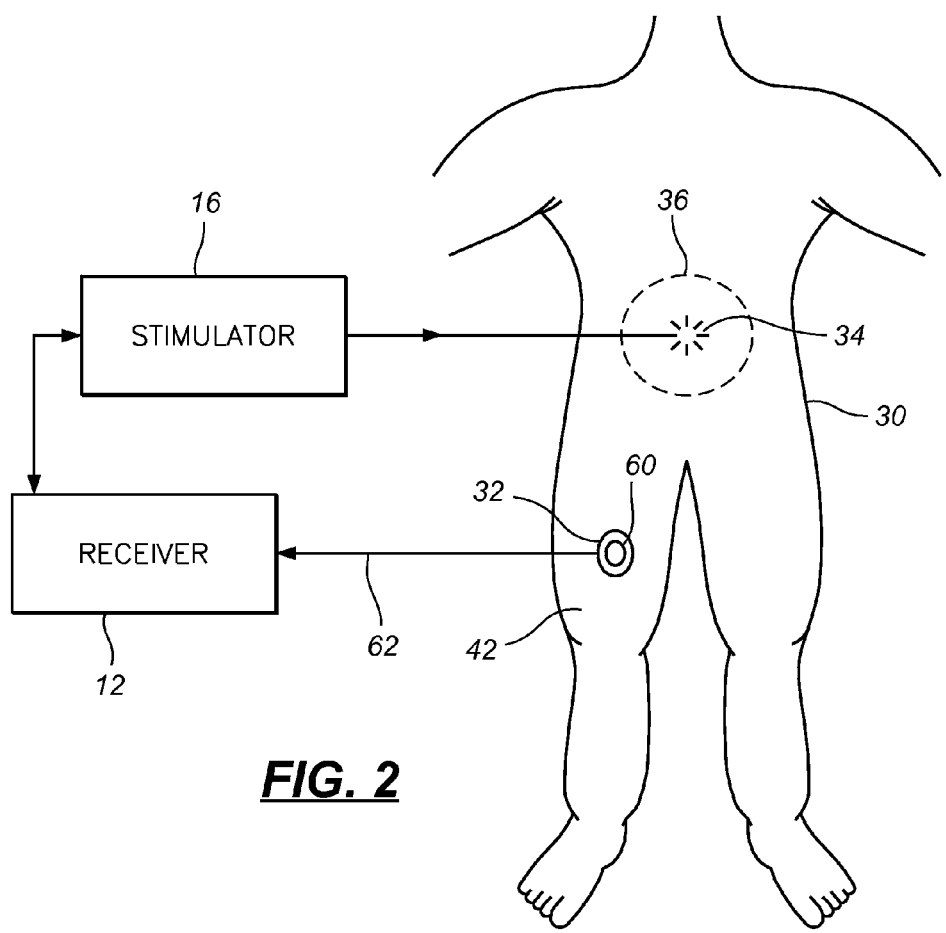
FIG. 2 is a schematic illustration of a mechanomyographic neural monitoring system used in conjunction with a human subject.

FIG. 2 schematically illustrates an embodiment of the neural monitoring system 10 being used together with a human subject 30. As shown, the neural monitoring system 10 includes a sensing device 32 (e.g., one of the plurality of sensing devices 14) in mechanical communication with one or more muscles of the subject 30. During a procedure, the stimulator 16 may be configured to provide a stimulus 34 within a treatment region 36 of the subject 30 where one or more nerves are expected to exist. The treatment region 36 may, for example, include the posterior, posterolateral, lateral, anterolateral or anterior regions of the lumbar or cervical spine, and/or the tissue surrounding such regions.

Figure 3:
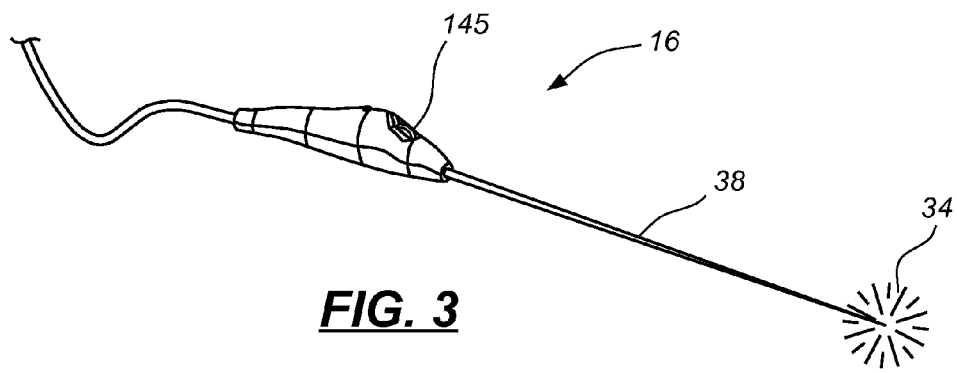
FIG. 3 is a perspective view of a stimulator that may be used to provide a stimulus to a treatment area within a subject.

As shown in FIGS. 3 and 4, the stimulator 16 may include a probe 38 or other invasive medical instrument that may be configured to extend within the treatment region 36 of the subject 30, and to provide a stimulus 34 therein. The stimulus 34 may be, for example, an electrical stimulus, though may alternatively be a thermal, chemical, ultrasonic, or infrared stimulus. Referring to FIG. 4, if the stimulus 34 is provided at, or sufficiently close to a nerve within the treatment region 36 (e.g., nerve 40), the stimulus 34 may be received by the nerve 40 in a manner that causes the nerve to depolarize. A depolarizing nerve may then induce a response in a muscle that is innervated by the nerve, which may then be detected by the sensing device 32. Examples of expected muscle responses may include, for example, physical motion, acceleration, displacement, or vibration of the muscle. While FIGS. 2 and 4 illustrate the treatment region 36 to include the lumbar spine, it is understood that the present invention may be used in connection with other surgical or therapeutic procedures that may be performed in the proximity of other peripheral motor nerves.

Referring again to FIG. 2, the one or more sensing devices 32 may be configured to detect mechanical and/or electrical responses of various muscles of the subject 30. In an embodiment, the sensing device 32 may be affixed to the skin of the subject 30 such that each sensor 32 is respectively in mechanical communication with a muscle innervated by a nerve within the treatment area 36. For example, as shown, the sensing device 32 may be placed in communication with a quadriceps muscle 42 of the subject 30 when the treatment area includes tissue surrounding the lumbar spine. As used herein, the sensing device 32 may be considered to be in mechanical communication with a muscle if it is sufficiently proximate to the muscle/muscle group to sense a mechanical response of the muscle.

By way of example, and not limitation, during a discectomy of the lumbar spine, a surgeon may know that the nerves exiting the L2, L3 and L4 foramen are potentially located in the treatment region 36. As illustrated in FIG. 5, the surgeon may place a sensing device 32 on each muscle innervated by those nerves. For instance, sensor devices 44, 46 may be placed on the vastus medialis muscles, which are innervated by nerves exiting the L2 and L3 foramens. Likewise sensors 48, 50 may be placed on the tibialis anterior muscles, which are innervated by the nerves exiting the L4 foramen.

Referring again to FIG. 2, in one configuration, the sensing device 32 may include an accelerometer 60 configured to monitor the mechanical motion of the adjacent muscle and to generate a corresponding mechanomyography (MMG) signal 62 in response. The receiver 12 may receive the MMG signal 62 through a wired or wireless communication link and may attempt to correlate any sensed motion to, for example, the stimulus 34 provided by the stimulator 16. To discern whether a sensed motion is an induced muscle response or an inadvertent movement of the muscle (e.g., an external bump), the receiver 12 may examine various characteristics of the MMG signal 62, such as peak magnitude and jerk (i.e., the time derivative of acceleration).

Figure 6:
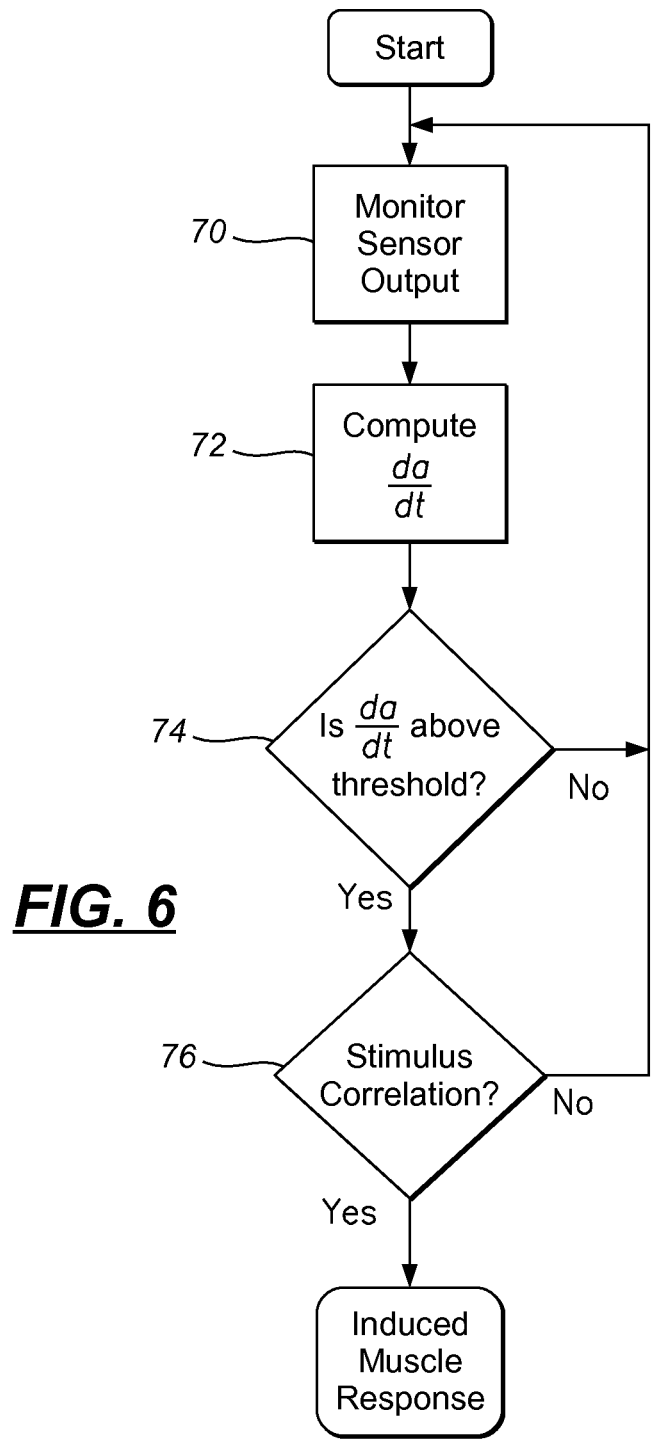
FIG. 6 is a flow diagram illustrating a method of detecting an induced muscle response.

As illustrated in FIG. 6, to detect an induced muscle response, the receiver 12 may first receive and register the raw readings of the accelerometer 60 in step 70 (e.g., via MMG signal 62). The receiver 12 may then use these raw readings to compute or derive the amount of muscle "jerk" experienced by the sensor in step 72 (i.e., "jerk," or a "jerk value," is the rate of change of the sensed acceleration (i.e. da/dt)). While a jerk value may be derived by taking the time derivative of acceleration, it may also be computed from other sensed mechanical parameters, such as velocity or position. It has been found that a muscle response induced by a provided stimulus may correspond to a particular jerk rate. By setting an appropriate threshold and comparing the derived jerk to the threshold (step 74), the system may be able to initially filter recorded readings to discriminate between a stimulator induced response, a patient-intended muscle movement, and an unintended environmental response (e.g. bumping the patient table).

A jerk threshold may be separately provided for each sensor at the discretion of the physician. In an embodiment, a local receiver may be included directly on each sensor device 32. In this configuration, the jerk threshold for each local receiver may be set/modified from a central control system, such as receiver 12. In such an embodiment, local event detection may operate by monitoring the mechanical and/or electrical response of the proximate muscle according to the associated thresholds. Additionally, each sensor may be configured to provide a visual or audible indication on the sensor itself if the individual thresholds are crossed and a muscle event is detected.

Figure 7:
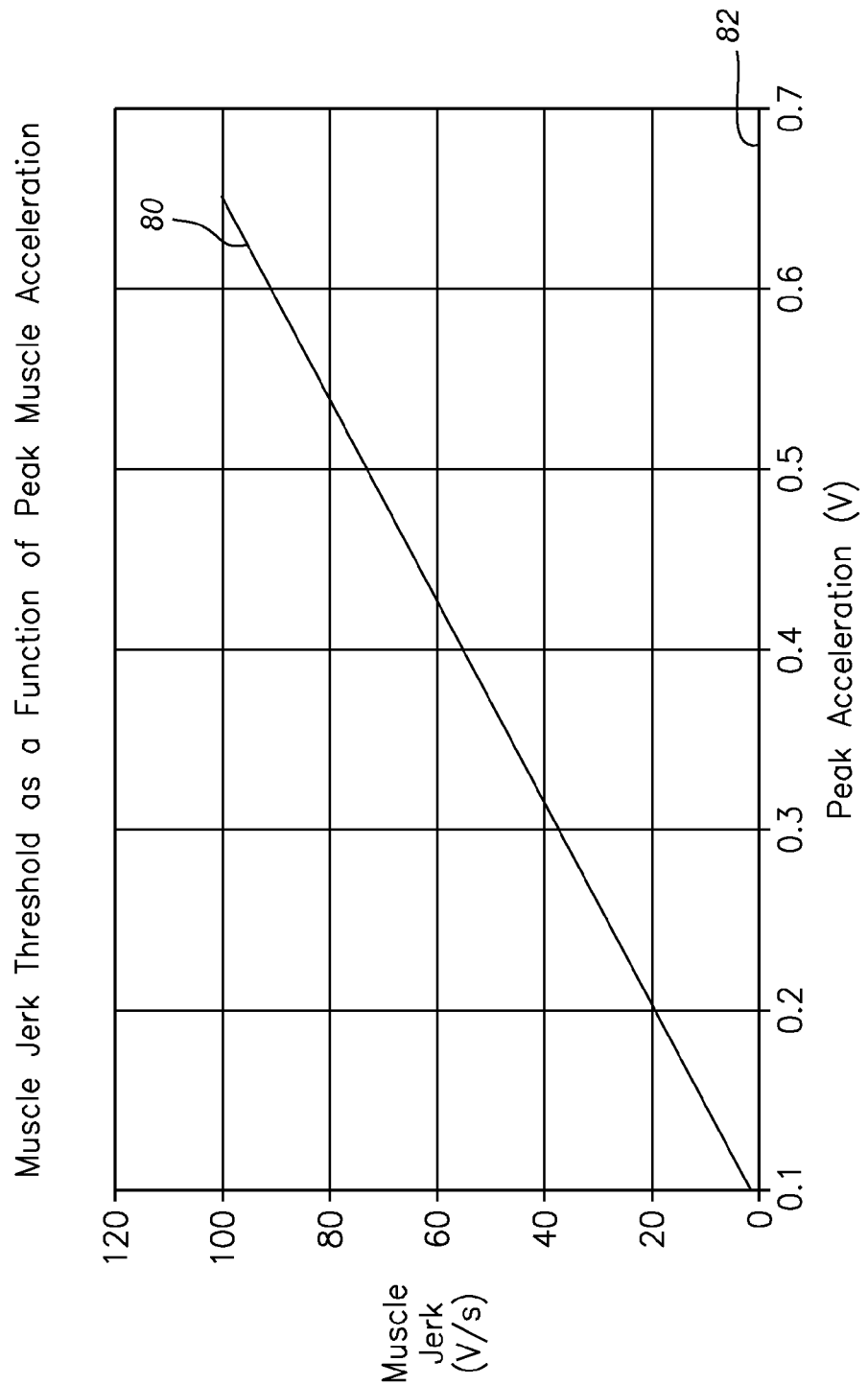
FIG. 7 is a graph illustrating a muscle jerk threshold as a function of peak muscle acceleration.

The jerk threshold used in step 74 for detecting an event may be varied based on the type or timing of the detected sensor response. For example, in an embodiment, as generally shown in FIG. 7, the jerk threshold 80 may be an increasing function of sensed accelerometer peak amplitude 82. In other embodiments, it may be a constant threshold.

In an embodiment where the stimulator 16 provides an electrical stimulus 34, the receiver 12 may further detect whether an electrical stimulus 34 was transmitted immediately prior to a sensed response/muscle jerk (e.g., in step 76). This correlation may allow the system to further relate a sensed muscle response to the physician's actions (further filtering out non-induced muscle responses). In other embodiments, other sensed or derived parameters may be used for the purpose of identifying stimulator-induced muscle response, as well as for testing the magnitude of the induced response.

The neural monitoring system 10 described above may be used to quantitatively assess and/or identify differences/changes in nerve function. As will be explained in greater detail below, when the stimulator 16 is placed in direct contact with (or immediately adjacent to) a nerve 40, the minimum stimulus 34 needed to induce a muscle event/response varies according to the health of the nerve 40. By determining, for example, the minimum electrical current required to induce a response, the system 10 may quantitatively compare a suspected injured nerve with a known healthy nerve. Alternatively, the system 10 may be used to analyze the efficacy of a decompression procedure by testing a nerve before and after the procedure.

Figure 8:
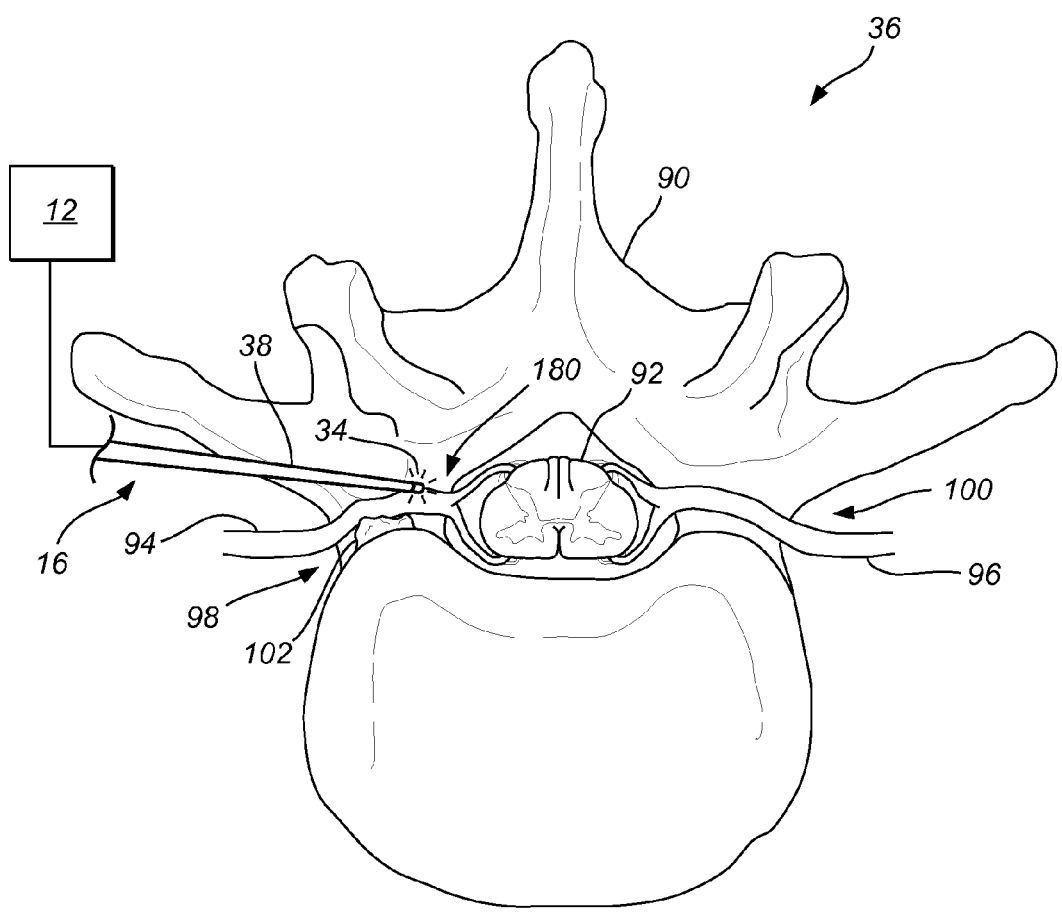
FIG. 8 is a schematic top view of a lumbar vertebrae including a neural foraminal stenosis.

FIG. 8 generally illustrates a portion of a treatment area 36 within a subject 30 that includes a lumbar vertebrae 90, spinal column 92, and a pair of nerve roots 94, 96 exiting the column 92 through vertebral foramen 98, 100 (i.e., natural passageways exiting the spinal canal). As illustrated, a bone spur 102 is compressing nerve root 94 against a portion of the foramen 98. Such a compression may reduce the nerve's ability to properly relay signals to the more peripherally located skeletal muscles.

Figure 9:
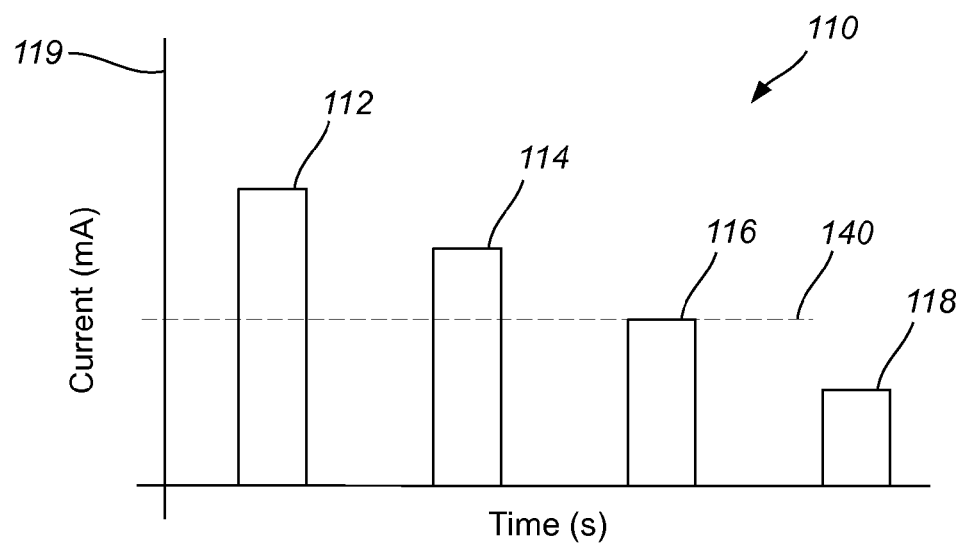
FIG. 9 is an electrical current graph of an electrical stimulus having a plurality of current pulses.

During the neural testing process, the receiver 12 may provide the stimulator 16 with an electrical stimulus 34, that may be conveyed via the stimulator probe 38 directly to the nerve 94. The stimulator probe 38 may either be in direct contact with the nerve 94, or may be in immediate proximate contact with the nerve 94 (i.e., contact through a minimal amount of fluid or tissue). FIG. 9 generally illustrates a current plot 110 of an electrical stimulus 34. As shown, the electrical stimulus 34 may include a plurality of sequentially administered pulses 112, 114, 116, 118 (e.g., at a 0.5-2.0 Hz frequency), with each respective pulse being provided with a different electrical current magnitude 119. While FIG. 9 illustrates direct current (DC) stimulus pulses, the pulses may also be alternating current (AC) pulses, with each pulse having a different root-mean-squared (RMS) current.

Figure 10:
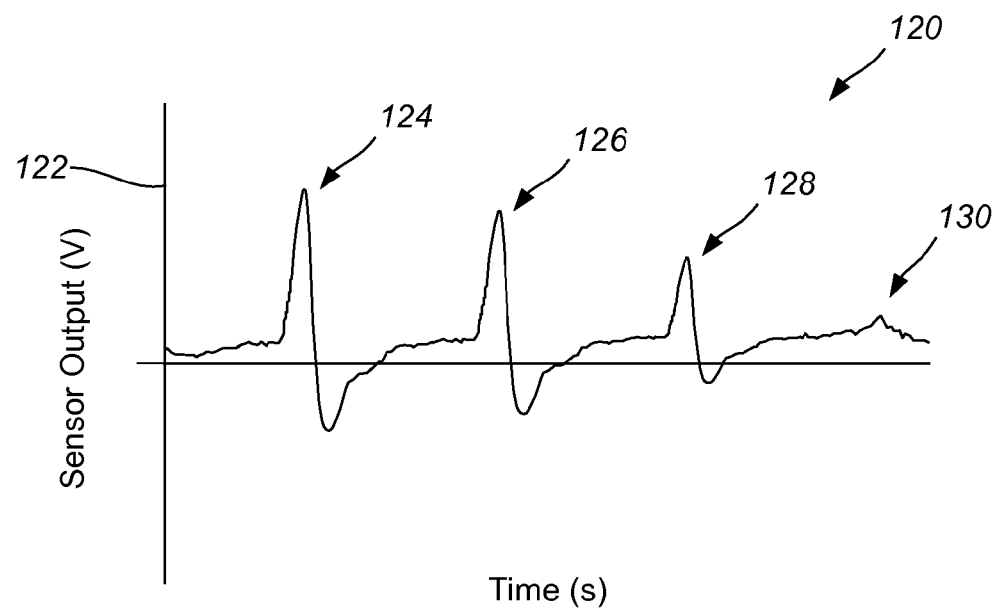
FIG. 10 is a graph of a mechanomyography signal, such as from an accelerometer in mechanical communication with a muscle of a subject, illustrating a plurality of muscle responses induced by an electrical stimulus of the kind provided in FIG. 9.

FIG. 10 then illustrates a graph 120 of a sensor output 122, such as may be received by the receiver 12 following the delivery of a stimulus 34 of the type provided in FIG. 9. As shown, the sensor output 122 may correspond to a muscle response detected by the accelerometer 60 and conveyed via the MMG signal 62. Using a detection method, such as described with respect to FIG. 6, the receiver 12 may determine that a muscle response was induced generally at 124, 126, 128, respectively corresponding with pulses 112, 114, 116. Conversely, the receiver 12 may fail to detect an induced response at 130 following pulse 118. From this empirical testing, the receiver 12 may determine the minimum electrical stimulus 140 required to induce a muscle response is the lowest provided current 119 at which an induced response was detected (given the pre-established detection thresholds). The minimum electrical stimulus 140 may be regarded as a threshold sensitivity, below which the nerve may not properly or fully depolarize to result in a muscle response.

In one configuration, the receiver 12 may employ a searching routine to locate and/or further refine the minimum electrical stimulus 140. For example, with reference to FIGS. 9-10, once identifying pulse 116 as the lowest provided current to induce a muscle response, the receiver 12 may then provide additional pulses at current levels between the currents of pulse 116 and pulse 118. In this manner, the minimum electrical stimulus 140 may be identified to within a pre-defined resolution. Furthermore, the current of the pulses of the stimulus 34 may be provided in either an increasing manner, or decreasing manner, or may be provided according to other searching schemes. In another configuration, the surgeon may manually increase and/or decrease the stimulus magnitude until the threshold minimum electrical stimulus 140 is detected. For example, the provided current 119 may be manually adjusted through a wheel 145 provided on the stimulator 16, such as shown in FIG. 3.

The minimum electrical stimulus 140 required to induce a muscle response for a particular nerve may be used to then assess the functioning of that particular nerve. For example, the minimum electrical stimulus 140 may be compared to a baseline established through direct testing of a subject's actual nerve, or through statistical data obtained from other subjects. In one configuration, the receiver 12 may compare the minimum electrical stimulus 140 required to induce a muscle response both before and after a decompression procedure to quantitatively assess the efficacy of the procedure. In another configuration, the receiver 12 may compare the minimum electrical stimulus 140 required to induce a muscle response for two separate nerves, for example, to quantitatively assess the degree to which one nerve may be impaired.

Figure 11:
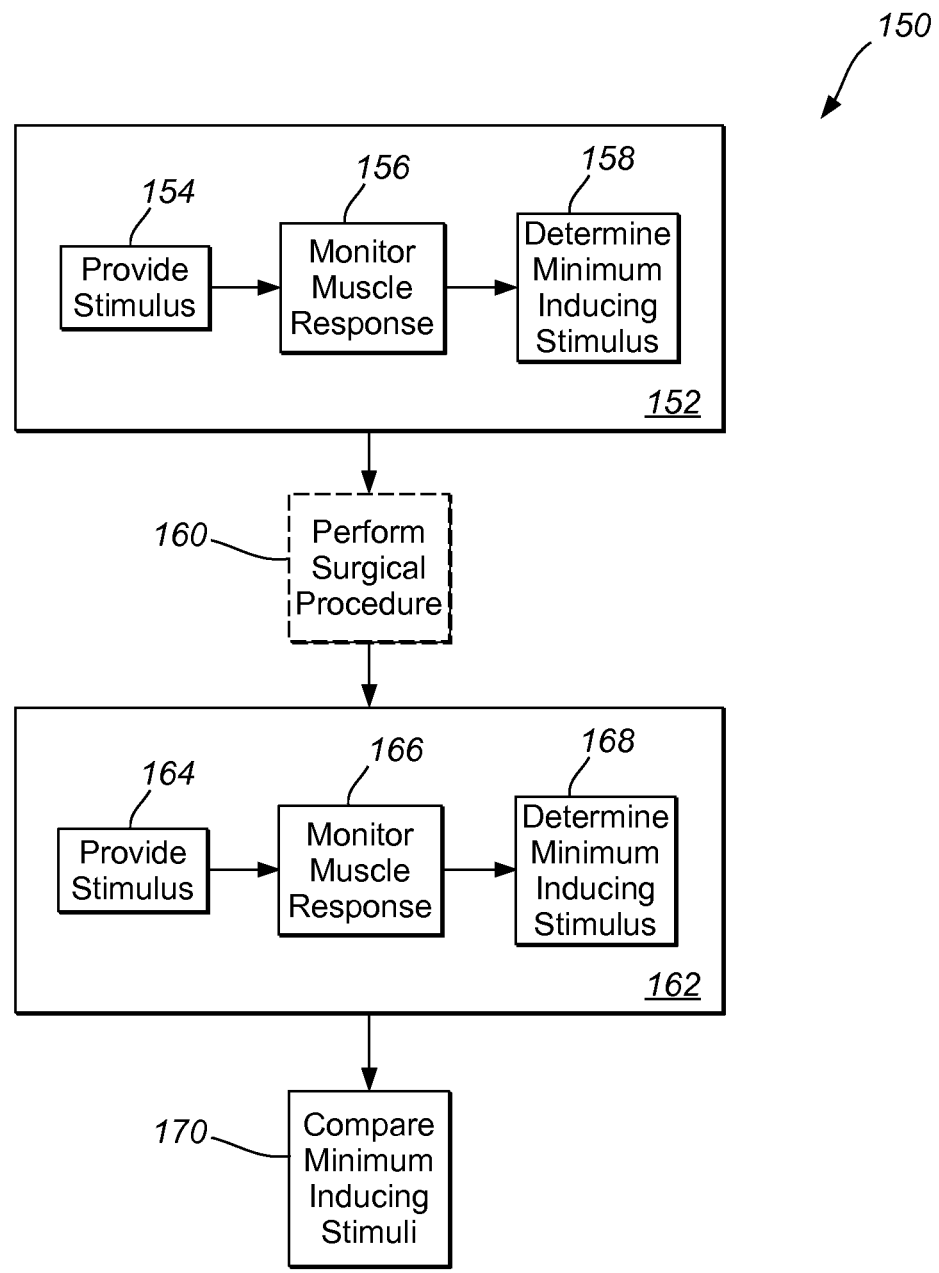
FIG. 11 is a flow diagram illustrating a method of identifying a change in nerve function attributable to a surgical procedure.

FIG. 11 illustrates a method 150 of quantitatively determining a difference in nerve function using this analysis technique. As illustrated, prior to the start of a surgical procedure 160, in step 152, the function of a nerve may be assessed to establish a baseline. Assessing the nerve function may include providing an electrical stimulus to the nerve (step 154), monitoring the mechanical motion of a muscle innervated by the nerve (step 156) (via the MMG signal 62 provided by the sensor/accelerometer 60), and determining a first, minimum electrical stimulus operative to induce the motion of the muscle (step 158)

Once this baseline threshold is determined, a surgeon may, for example, perform a decompression procedure (step 160) to alleviate an impingement of the nerve. Depending on the nature of the neural compression, different surgical decompression procedures may be employed. For example, the decompression procedure may involve removing a bone spur 102 or herniated disk that may be protruding into a nerve root 94. Step 160 is provided in phantom in FIG. 11 to identify that it is not a necessary element of the method 150, and therefore, should not be read to limit the present invention unless explicitly noted as such.

Following the decompression procedure (step 160), the nerve function of the, now decompressed, nerve may be reassessed (step 162) using the same procedure. That is, the nerve may be reassessed by providing an electrical stimulus to the nerve (step 164), monitoring the mechanical motion of a muscle innervated by the nerve (step 166) (via the MMG signal provided by the sensor/accelerometer), and determining a second, minimum electrical stimulus operative to induce the motion of the muscle (step 168).

Once the nerve function has been reassessed, the receiver may quantitatively determine a change in nerve function (step 170) by comparing the first minimum electrical stimulus (i.e., the baseline), determined in step 158, with the second minimum electrical stimulus, determined in step 168. For example, the change may be determined by subtracting the current level of the second, minimum electrical stimulus from the current level of the first, minimum electrical stimulus. The magnitude of the decrease from the baseline may indicate the degree of improvement in nerve sensitivity, and correspondingly, nerve function.

In an embodiment, the stimulus provided in both step 154 and step 164 may be provided to the nerve in roughly the same location along the nerve. Additionally, as illustrated in FIG. 8, the stimulus may be provided at a location 180 along the nerve, which lies generally between the impingement (e.g., bone spur 102) and the spinal column 92. In this manner, the impingement/compression may lie between the stimulated portion of the nerve and the more peripherally located sensor.

In another configuration, the method 150 may be used to quantitatively assess differences in nerve function between two different nerves. For example, in a trauma scenario, a surgeon may first assess the functioning of a known healthy nerve to establish a baseline for neural function within the subject. The surgeon may then systematically assess nerves within the trauma area to determine any impaired functioning, attributable to the trauma. If the minimum electrical stimulus required to induce a muscle response via the known healthy nerve is different than the minimum electrical stimulus required for a subsequently tested nerve, the receiver 10 may indicate an impairment. In this manner, the surgeon may be better guided to the degree and location of a necessary decompression.

Figure 12:
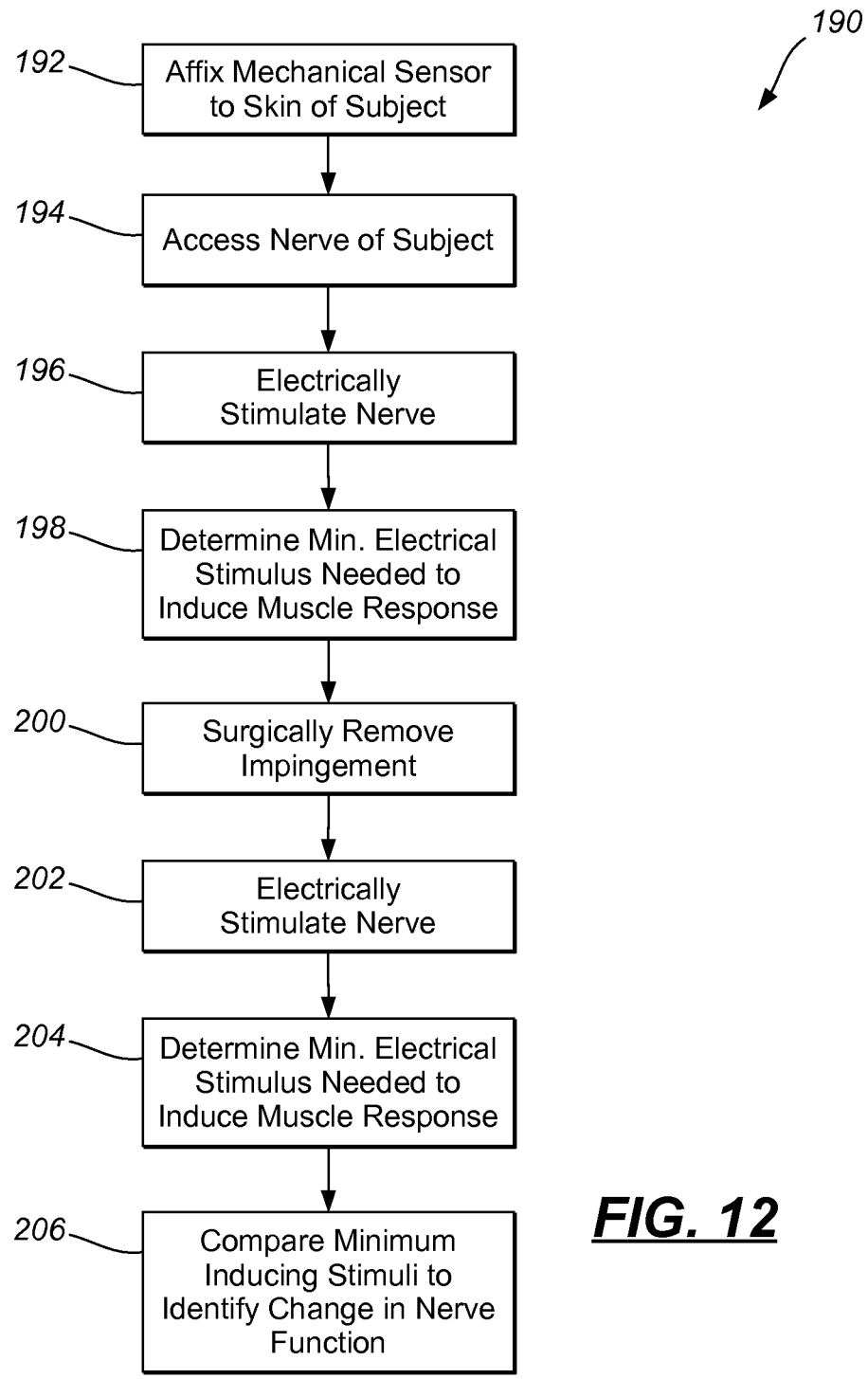
FIG. 12 is a flow diagram illustrating a neurosurgical method.

FIG. 12 illustrates a neurosurgical method 190 using the aforementioned assessment techniques. The method 190 begins at step 192 by affixing a mechanical sensor to the skin of a subject and in mechanical communication with a muscle innervated by a nerve, such that the mechanical sensor is configured to monitor the motion of the muscle. In step 194, a surgeon may then obtain direct access to the nerve, where the nerve, for example, has an impingement. In step 196, the surgeon may electrically stimulate the nerve with a first electrical stimulus at a location between the impingement and a spinal column of the subject. Using the output of the mechanical sensor, in step 198, the surgeon may determine a first, minimum electrical stimulus operative to induce motion of the muscle. This first, minimum electrical stimulus, may be for example, a minimum electrical current that must be provided to the nerve to cause the muscle jerk to exceed a predefined threshold. Additionally, the first, minimum electrical stimulus may serve as the baseline for future tests.

Using known surgical techniques, in step 200, the surgeon may surgically remove the impingement from the nerve to decompress the nerve. Following the decompression, in step 202, the surgeon may electrically stimulate the nerve with a second electrical stimulus proximate to where the first electrical stimulus was administered (e.g., between the location of the removed impingement and the spinal column of the subject). In step 204, the surgeon may determine, from the output of the mechanical sensor, a second, minimum electrical stimulus operative to induce motion of the muscle. In step 206, the surgeon may identify a change in nerve function if the second, minimum electrical stimulus is different than the first, minimum electrical stimulus. Furthermore, the surgeon may determine the degree of the change (e.g., via a percent improvement) from the magnitude of the respective first and second minimum electrical stimuli.

Figure 13:
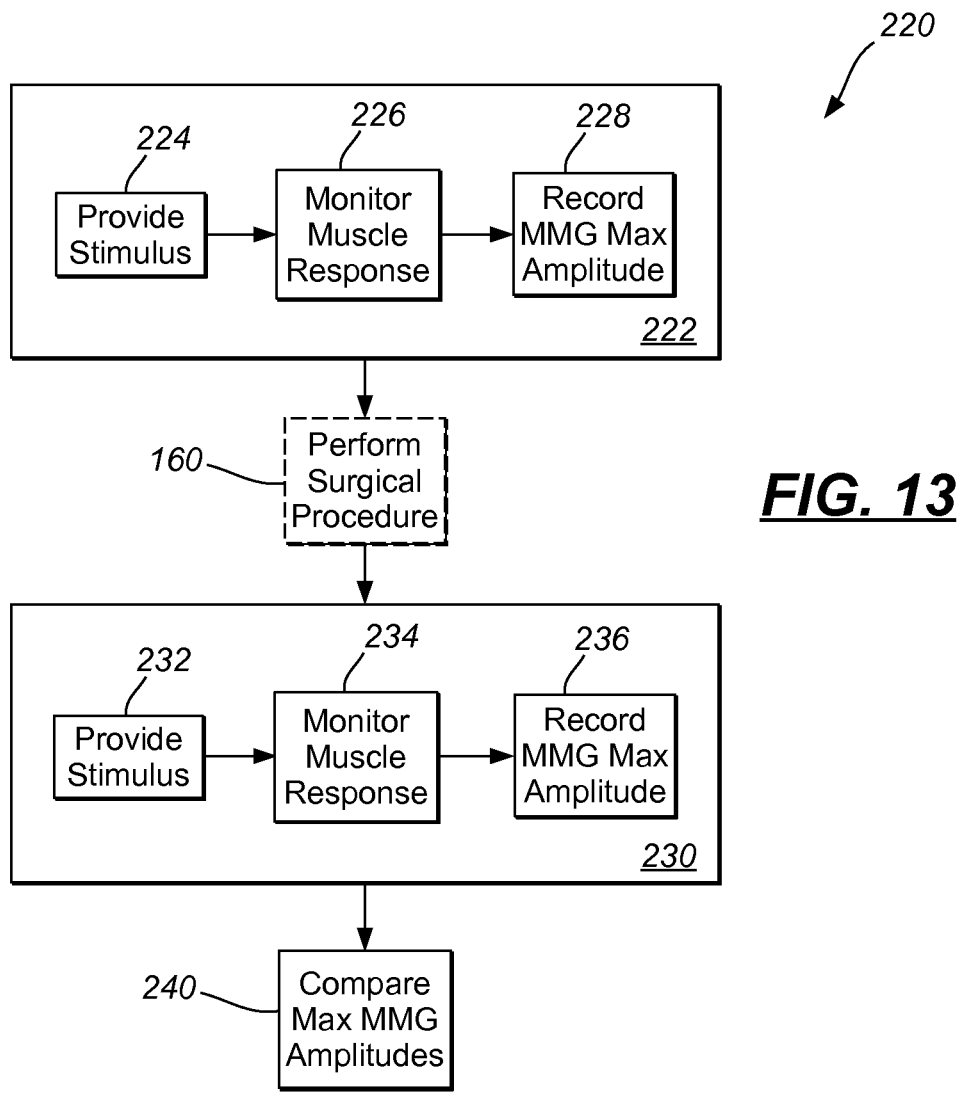
FIG. 13 is a flow diagram illustrating a method of identifying a change in nerve function attributable to a surgical procedure.

In another configuration, such as illustrated in FIG. 13 and described below, a method 220 of quantitatively determining a difference in nerve function may involve providing a stimulus having a fixed current, before and after a procedure, and monitoring the received MMG signal for differing amplitude responses. As illustrated, prior to the start of a surgical procedure 160, in step 222, the function of a nerve may be assessed to establish a baseline. Assessing the nerve function may include providing a fixed current electrical stimulus to the nerve (step 224), monitoring the mechanical motion of a muscle innervated by the nerve for an induced muscle response (step 226) (via the MMG signal 62 provided by the sensor/accelerometer 60), and recording the maximum amplitude of the MMG signal 62 during the induced muscle response (step 228). A fixed current electrical stimulus, such as used in step 226, may include one or more electrical pulses that are all provided at a single current level, which is greater than the minimum electrical stimulus operative to induce the motion of the muscle.

Once this baseline threshold is determined, a surgeon may, for example, perform a decompression procedure (step 160) to alleviate an impingement of the nerve. Step 160 is provided in phantom in FIG. 13 to identify that it is not a necessary element of the method 220, and therefore, should not be read to limit the present invention unless explicitly noted as such.

Following the decompression procedure (step 160), the nerve function of the, now decompressed, nerve may be reassessed (step 230) using the same procedure described in step 222. That is, the nerve may be reassessed by providing the same fixed current electrical stimulus to the nerve (step 232), monitoring the mechanical motion of a muscle innervated by the nerve for an induced muscle response (step 234) (via the MMG signal provided by the sensor/accelerometer), and recording the maximum amplitude of the MMG signal 62 during the induced muscle response (step 236).

Figure 14:
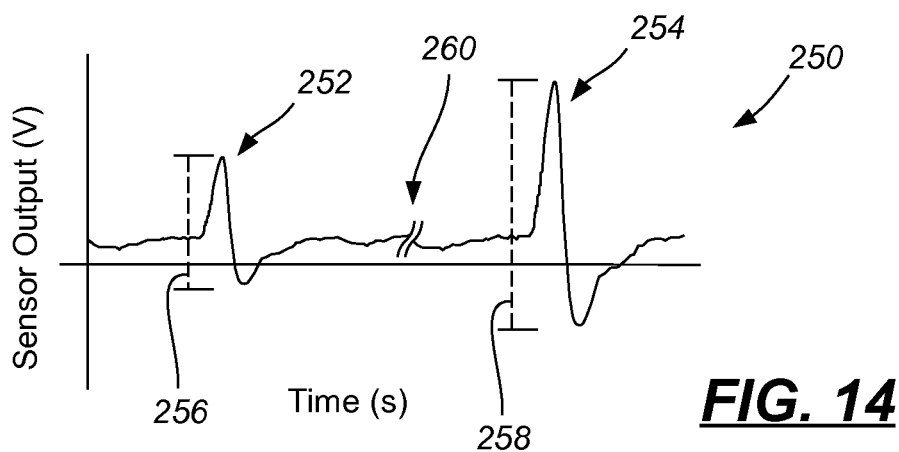
FIG. 14 is a graph of a mechanomyography signal, such as from an accelerometer in mechanical communication with a muscle of a subject, illustrating a first and a second muscle response.

Once the nerve function has been reassessed, the receiver may quantitatively determine a change in nerve function (step 240) by comparing the first maximum MMG amplitude (i.e., the baseline), recorded in step 228, with the second maximum MMG amplitude, recorded in step 236. For example, FIG. 14 illustrates an MMG signal trace 250 having a first MMG signal 252, which may be monitored before a procedure (i.e., in step 226), and a second MMG signal 254, which may be monitored after a procedure (i.e., in step 234). Both MMG signals 252, 254 may have been induced by a respective electrical stimulus having a similar magnitude, fixed current. As shown, the first MMG signal may have a first maximum amplitude or range 256, and the second MMG signal 256 may have a second maximum amplitude or range 258. As further illustrated, a decompression procedure may have been performed generally at a time 260 between the two signals 252, 254.

By comparing the first maximum amplitude or range 256 with the second maximum amplitude or range 258, a surgeon may be able to quantitatively assess the efficacy of the decompression procedure. For example, as shown in FIG. 14, the MMG muscle response has increased following the procedure, thus indicating a corresponding improvement in nerve sensitivity, and correspondingly, nerve function.

While the best modes for carrying out the invention have been described in detail, those familiar with the art to which this invention relates will recognize various alternative designs and embodiments for practicing the invention within the scope of the appended claims. It is intended that all matter contained in the above description or shown in the accompanying drawings shall be interpreted as illustrative only and not as limiting.

The invention claimed is:

1. A method of quantitatively identifying a difference in nerve function, the method comprising:
   generating a first electrical stimulus;
   receiving a first mechanomyography signal from an accelerometer in mechanical communication with a muscle of a subject, the first mechanomyography signal indicative of a mechanical muscle response induced by the first electrical stimulus;
   recording a maximum amplitude of the received, first mechanomyography signal;
   generating a second electrical stimulus receiving a second mechanomyography signal from the accelerometer, the second mechanomyography signal indicative of a mechanical muscle response induced by the second electrical stimulus;
   recording a maximum amplitude of the received, second mechanomyography signal;
   identifying a difference in nerve function if the maximum amplitude of the received, second mechanomyography signal is different than the maximum amplitude of the received, first mechanomyography signal;
   wherein the first electrical stimulus and the second electrical stimulus have a common current; and
   wherein the difference in nerve function is attributable to a surgical procedure.

2. The method of claim 1, further comprising providing each of the respective first and second electrical stimuli to the distal end portion of a stimulator that is configured to extend within an intracorporeal treatment area of the subject.

3. The method of claim 1, wherein the accelerometer is disposed external to the subject.

4. The method of claim 3, further comprising affixing the accelerometer to an external skin surface of the subject.

5. The method of claim 1, further comprising calculating a difference between the maximum amplitude of the second mechanomyography signal and the maximum amplitude of the first mechanomyography signal.

6. The method of claim 1, further comprising: transmitting the first electrical stimulus from a stimulator to tissue of the subject within the intracorporeal treatment region; and
   transmitting the second electrical stimulus from the stimulator to the tissue within the intracorporeal treatment region.

7. A method of identifying a change in nerve function for a nerve that extends within an intracorporeal treatment region of a subject and innervates a muscle of the subject, the method comprising:
   providing a first electrical stimulus via a stimulator at a first time;
   monitoring a first mechanical response of the muscle to the first electrical stimulus;
   recording a maximum amplitude of the first mechanical response of the muscle to the first electrical stimulus;
   providing a second electrical stimulus via the stimulator at a second time;
   monitoring a second mechanical response of the muscle to the second electrical stimulus;
   recording a maximum amplitude of the second mechanical response of the muscle to the second electrical stimulus;
   identifying a change in nerve function if the maximum amplitude of the second mechanical response is different than the maximum amplitude of the first mechanical response; and
   wherein the change in nerve function is attributable to a surgical procedure.

8. The method of claim 7, further comprising calculating a difference between the maximum amplitude of the second mechanical response and the maximum amplitude of the first mechanical response.

9. The method of claim 7, wherein monitoring the first mechanical response of the muscle and monitoring the second mechanical response of the muscle each respectively include:
   generating a mechanomyography output signal from a non-invasive mechanical sensor configured to be disposed in mechanical communication with the muscle of the subject; and
   wherein the mechanomyography output signal corresponds to a mechanical movement of the muscle.

10. The method of claim 7, wherein the first electrical stimulus and the second electrical stimulus are each respectively provided at a common current.

11. The method of claim 7, wherein the stimulator is an invasive medical instrument configured to extend within the intracorporeal treatment region;
   wherein providing the first electrical stimulus via the stimulator includes transmitting a first electrical current from the stimulator to tissue of the subject within the intracorporeal treatment region; and
   wherein providing the second electrical stimulus via the stimulator includes transmitting a second electrical current from the stimulator to the tissue within the intracorporeal treatment region.

12. A neural monitoring system for determining a change in the function of a nerve of a subject over a period of time, the system comprising:
   a stimulator configured to extend within an intracorporeal treatment region of the subject and to provide an electrical stimulus therein;
   a non-invasive mechanical sensor configured to be placed in communication with a muscle of the subject and to generate a mechanomyography output signal corresponding to a response of the muscle to the electrical stimulus;
   a processor in communication with the stimulator and with the sensor, the processor configured to:

provide a first electrical stimulus via the stimulator at a first time;
determine a first amplitude of the mechanomyography output signal that corresponds to a response of the muscle to the first electrical stimulus;
provide a second electrical stimulus via the stimulator at a second time;
determine a second amplitude of the mechanomyography output signal that corresponds to a response of the muscle to the second electrical stimulus;
indicate a change in the function of the nerve to a user, the indication corresponding to the difference between the first amplitude and the second amplitude;
wherein the change in nerve function is attributable to a surgical procedure.

13. The system of claim 12, wherein the first electrical stimulus and the second electrical stimulus are each respectively provided at a common current.

14. The system of claim 12, wherein the stimulator is an invasive medical instrument.

15. The system of claim 12, wherein each of the first and second electrical stimuli include a respective current pulse.

16. The system of claim 12, wherein the non-invasive mechanical sensor includes an accelerometer.

* * * * *

UNITED STATES PATENT AND TRADEMARK OFFICE
CERTIFICATE OF CORRECTION

| | | |
|---|---|---|
| PATENT NO. | : 8,983,593 B2 | Page 1 of 1 |
| APPLICATION NO. | : 13/293389 | |
| DATED | : March 17, 2015 | |
| INVENTOR(S) | : Stephen Bartol et al. | |

It is certified that error appears in the above-identified patent and that said Letters Patent is hereby corrected as shown below:

In the Claims

Column 9, line 54:

The second occurrence of the word "the" should be replaced with the word "a" so that line 54 should read: "each of the respective first and second electrical stimuli to a".

Signed and Sealed this
Fifteenth Day of September, 2015

Michelle K. Lee
*Director of the United States Patent and Trademark Office*